US008506521B1

(12) United States Patent
Teves

(10) Patent No.: US 8,506,521 B1
(45) Date of Patent: Aug. 13, 2013

(54) ADAPTOR FOR CONNECTING A CANNULA TO A GAS MACHINE

(76) Inventor: Leonides Y. Teves, Bradenton, FL (US)

(*) Notice: Subject to any disclaimer, the term of this patent is extended or adjusted under 35 U.S.C. 154(b) by 748 days.

(21) Appl. No.: 12/409,721

(22) Filed: Mar. 24, 2009

Related U.S. Application Data

(63) Continuation-in-part of application No. 12/132,395, filed on Jun. 3, 2008, now abandoned, which is a continuation-in-part of application No. 11/935,813, filed on Nov. 6, 2007, now abandoned.

(51) Int. Cl.
*A61M 37/00* (2006.01)

(52) U.S. Cl.
USPC .......... 604/26; 604/506

(58) Field of Classification Search
USPC .......... 604/23–26, 43, 500, 506, 511–513
See application file for complete search history.

(56) References Cited

U.S. PATENT DOCUMENTS

| | | | | |
|---|---|---|---|---|
| 3,468,445 | A * | 9/1969 | Ballin | 215/11.6 |
| 5,411,491 | A * | 5/1995 | Goldhardt et al. | 604/247 |
| 5,487,727 | A * | 1/1996 | Snider et al. | 604/508 |
| 5,941,852 | A | 8/1999 | Dunlap et al. | |
| 5,957,902 | A | 9/1999 | Teves | |
| 6,685,665 | B2 | 2/2004 | Booth et al. | |
| 6,872,196 | B1 * | 3/2005 | Bryan | 604/305 |
| 7,172,085 | B2 * | 2/2007 | Beaudette | 215/11.1 |
| 2001/0020146 | A1 * | 9/2001 | Satterfield et al. | 604/24 |
| 2002/0008386 | A1 * | 1/2002 | Lee | 285/322 |
| 2007/0088274 | A1 * | 4/2007 | Stubbs et al. | 604/164.01 |
| 2008/0294090 | A1 * | 11/2008 | Heath | 604/26 |

* cited by examiner

*Primary Examiner* — Kami A Bosworth

(74) *Attorney, Agent, or Firm* — Ronald E. Smith; Smith & Hopen, P.A.

(57) ABSTRACT

A cannula for delivering gas to an abdominal cavity includes a tubular main body that defines a lumen. A hub is formed at the proximal end of the main body and a central bore is formed in the hub. An annular groove is formed in an outer periphery of the hub. A nipple has a radially-inwardly extending annular ridge formed in it and the diameter of the annular ridge is slightly less than a diameter of the annular groove so that the annular groove releasably but snugly receives the annular ridge. An elongate hose is adapted to provide fluid communication between a remote gas machine and an enclosed space defined by the nipple and the hub when the nipple is attached to the hub. Gas under pressure is delivered to an abdominal cavity of a patient through the hose, the enclosed space, and the lumen.

16 Claims, 7 Drawing Sheets

10
14
20
11
24
12
32
16
30
26
28

11
28
12
18
26
14
20
22
16
30
10
24
32

10
11
12
16
22
24
26
28
30
40
40a
40b 6
6
40
26
30
24
14
20

12
18
42
5
5

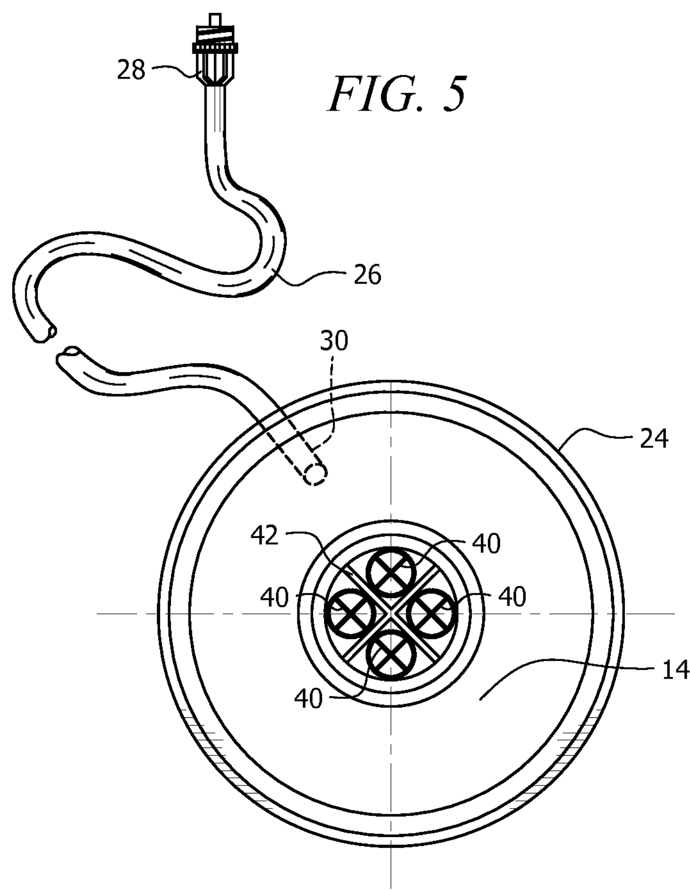
*FIG. 5*
*FIG. 6*
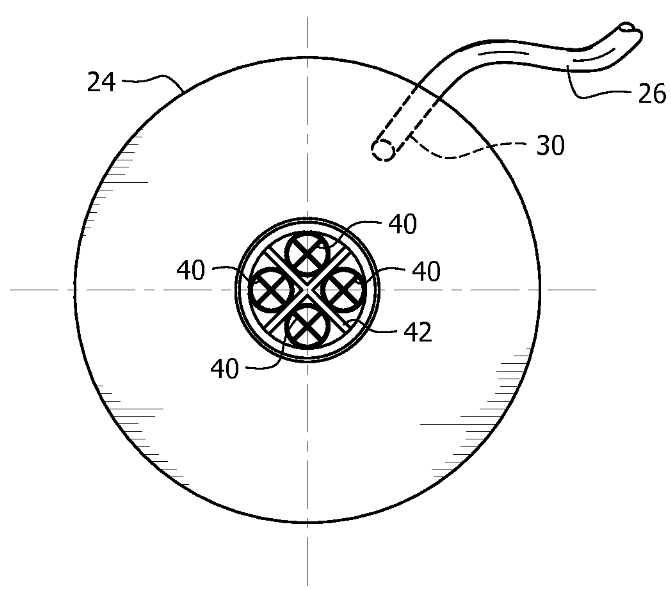

ADAPTOR FOR CONNECTING A CANNULA TO A GAS MACHINE

CROSS REFERENCE TO RELATED APPLICATIONS

This application is a continuation-in-part of co-pending U.S. patent application Ser. No. 12/132,395, filed Jun. 3, 2008, which is a continuation-in-part of co-pending U.S. patent application Ser. No. 11/935,813, filed Nov. 6, 2007, both of which have the same inventor and both of which are entitled "Adaptor for Connecting Cannula to Gas Machine."

BACKGROUND OF THE INVENTION

1. Field of the Invention

This invention relates, generally, to surgical tools. More particularly, it relates to an adaptor for cannulas used in laparoscopic surgery.

2. Description of the Prior Art

The size of an incision is minimized in laparoscopic surgery so that post-operative recovery is faster and less painful than conventional large incision surgery. A trocar is a tube-like tool that is inserted into a small incision; it can be left in position so that its lumen provides a passageway for other surgical tools that are used in the course of a surgical procedure. This avoids the trauma that would be associated with insertion and withdrawal of various instruments during the course of the surgery.

U.S. Pat. No. 5,957,902 to the present inventor provides an improved trocar. Before the invention of the improved trocar it was sometimes necessary to remove a relatively small diameter trocar from an incision and to insert a larger one. This defeats the purpose of a trocar which is to minimize multiple withdrawals and insertion of instruments through an incision. The invention disclosed in the referenced patents thus provides a trocar having a diameter that can be increased without requiring withdrawal of the trocar.

A trocar has utility, for example, where gas under pressure must be introduced into a patient's abdominal cavity. An elongate hose is employed to provide fluid communication between a remote gas machine and a cannula, and the cannula is introduced into the abdominal cavity through the lumen of the trocar. Adaptors for interconnecting the hose to a proximal end of the cannula are commercially available, but they are relatively expensive because they are made from multi-cavity molds. If the connection is not secure, the hose may separate from the proximal end of the cannula.

Accordingly, there is a need for an improved adaptor that is relatively inexpensive and easy to use. The improved adaptor should be substantially leak free and it should securely engage the cannula so that the cannula is not easily disconnected from the gas machine during surgery.

There is also a need for an adaptor having utility with conventional trocars as well.

However, in view of the art considered as a whole at the time the present invention was made, it was not obvious to those of ordinary skill in this art how the identified needs could be met.

SUMMARY OF INVENTION

The long-standing but heretofore unfulfilled need for an improved assembly for delivering gas to the abdominal cavity of a patient in the substantial absence of leakage is now met by a new, useful, and nonobvious invention. The novel assembly includes a cannula formed by an elongate, tubular main body that defines a lumen. A disc-shaped hub is formed at the proximal end of the tubular main body and a central aperture is formed in the hub. The proximal end of the cannula is slideably received within the central aperture.

An annular groove is formed in the outer periphery of the disc-shaped hub.

A baby bottle nipple formed of a flexible and resilient material has a radially-inwardly extending annular ridge formed therein. The annular ridge has a diameter slightly less than a diameter of the annular groove so that the annular groove releasably but snugly receives the annular ridge.

In a first embodiment, the nipple has an elongate, narrow proximal end and a wide distal end that engages the annular groove formed in the periphery of the hub. A valve adapted to sealingly engage a surgical instrument is formed in the narrow proximal end at its tip.

The use of a conventional baby bottle nipple is highly advantageous in that it performs the work of sealing the gas against escape at a cost much lower than that of conventional adaptors that provide a similar seal.

An elongate hose is adapted to provide fluid communication between a remote gas machine and a space defined by the nipple and the disc-shaped hub when the nipple is attached to the disc-shaped hub, i.e., the interior of the nipple. A hose connector is secured to a proximal end of the elongate hose and is adapted to engage the remote gas machine. Gas under pressure follows a path of travel from an outlet port of the gas machine, through a stopcock or other suitable valve, the lumen of the elongate hose, through an opening formed in the nipple into the enclosed space defined by the nipple as it engages the hub, into the lumen of the cannula, and into the abdominal space.

The annular groove formed in the periphery of the hub has a substantially square contour in transverse cross-section and the annular ridge formed in the nipple has a mating, substantially square contour in transverse cross-section. An adhesive may be applied to the annular groove or annular ridge to enhance the seal between them.

In a second embodiment, the narrow proximal end of the nipple is cut off at its base where it joins the wide distal end so that a circular opening is formed in the nipple. A valve adapted to sealingly engage at least one surgical instrument is placed in that opening. More particularly, the valve is adapted to seal around the periphery of a surgical instrument to inhibit leakage of gas when a surgical instrument is positioned in the lumen of the cannula. The valve also seals the nipple against gas leakage when a surgical instrument is withdrawn from the valve. Any suitable one way valve may be formed in the nipple.

In a third embodiment, four (4) valves adapted to sealingly engage surgical instruments are placed in the circular opening created by cutting off the narrow proximal end of the nipple at said base. This invention includes a lesser or greater number of valves.

In the third embodiment, the lumen of the cannula is preferably subdivided so that a different instrument can be inserted into each subdivision of the lumen. As an example, the lumen is divided into four (4) lumens so that a total of four (4) instruments may be inserted. This requires the valve means that sealingly engages a preselected surgical instrument to include four (4) independently formed valves. One of the instruments may be a camera, for example, another may be an illumination means, another may be an irrigation means, and so forth.

In all embodiments, a small gas-access opening is formed in the nipple and a compression fitting extends snugly through said gas-access opening. The fitting includes a base having a diameter substantially greater than a diameter of the gas-access opening and a post formed integrally with the base. The post has a diameter greater than a diameter of the lumen of the elongate hose. The base is positioned within the space defined by the disc-shaped hub and the nipple and the post is positioned externally of the nipple. At least one annular ridge is formed on the post and is angled to facilitate sliding attachment of the distal end of the elongate hose onto the post but to prevent facile detachment of the distal end from the post.

An important object of the invention is to provide a low cost way of interconnecting a gas machine and a cannula.

A more specific object is to interconnect a gas machine and a cannula by using a staple item of commerce such as a baby bottle nipple.

Another object is to perform the same function without a baby bottle nipple so that the adaptor has a very simple and inexpensive structure.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 5 is an end view taken along line 5-5 in FIG. 4; and

FIG. 6 is an end view taken along line 5-5 in FIG. 4.

DETAILED DESCRIPTION OF THE PREFERRED EMBODIMENT

Figure 1A:
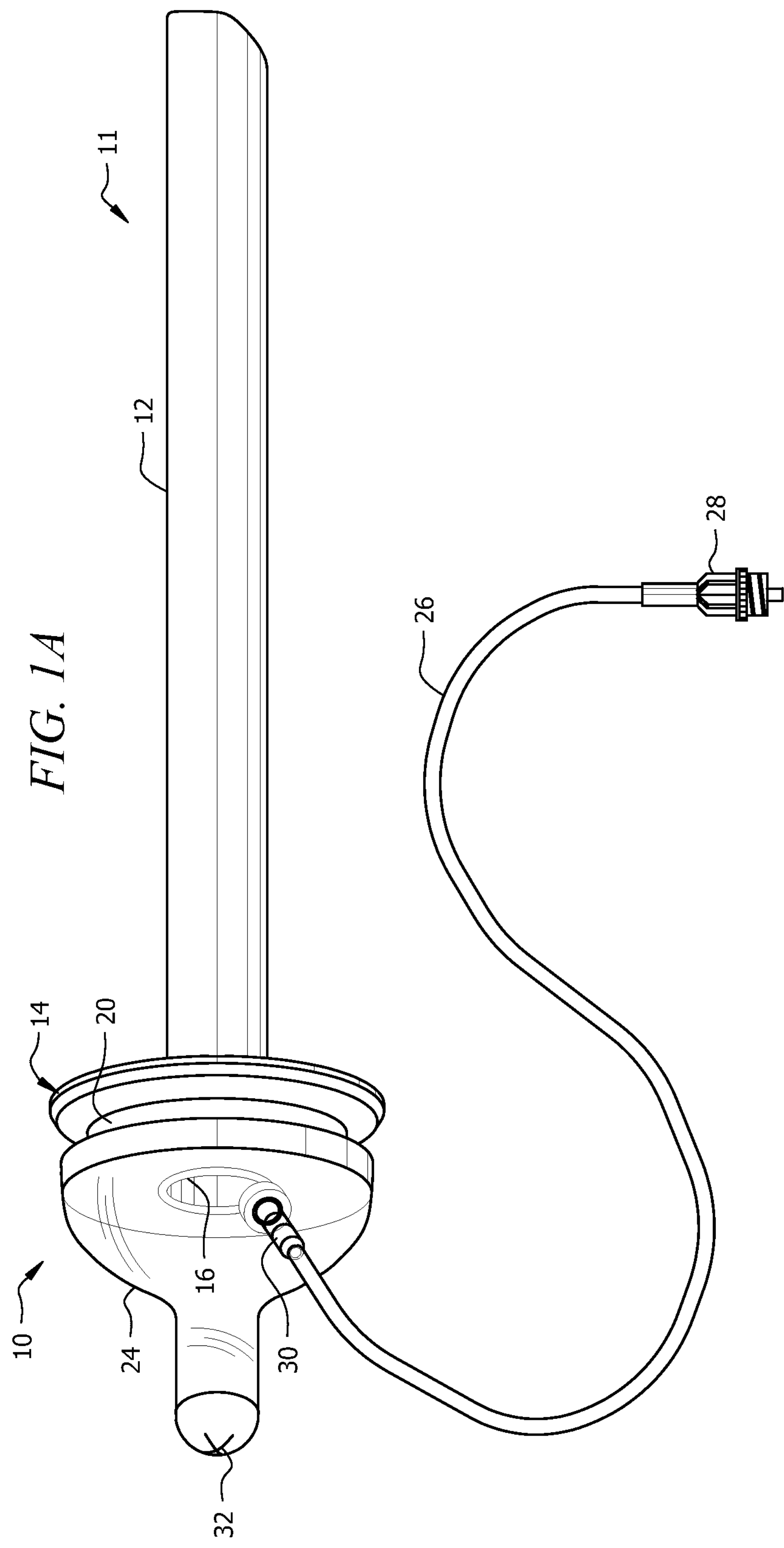
FIG. 1A is a first, frontal perspective view of a first embodiment of the novel cannula and trocar assembly.
Figure 1B:
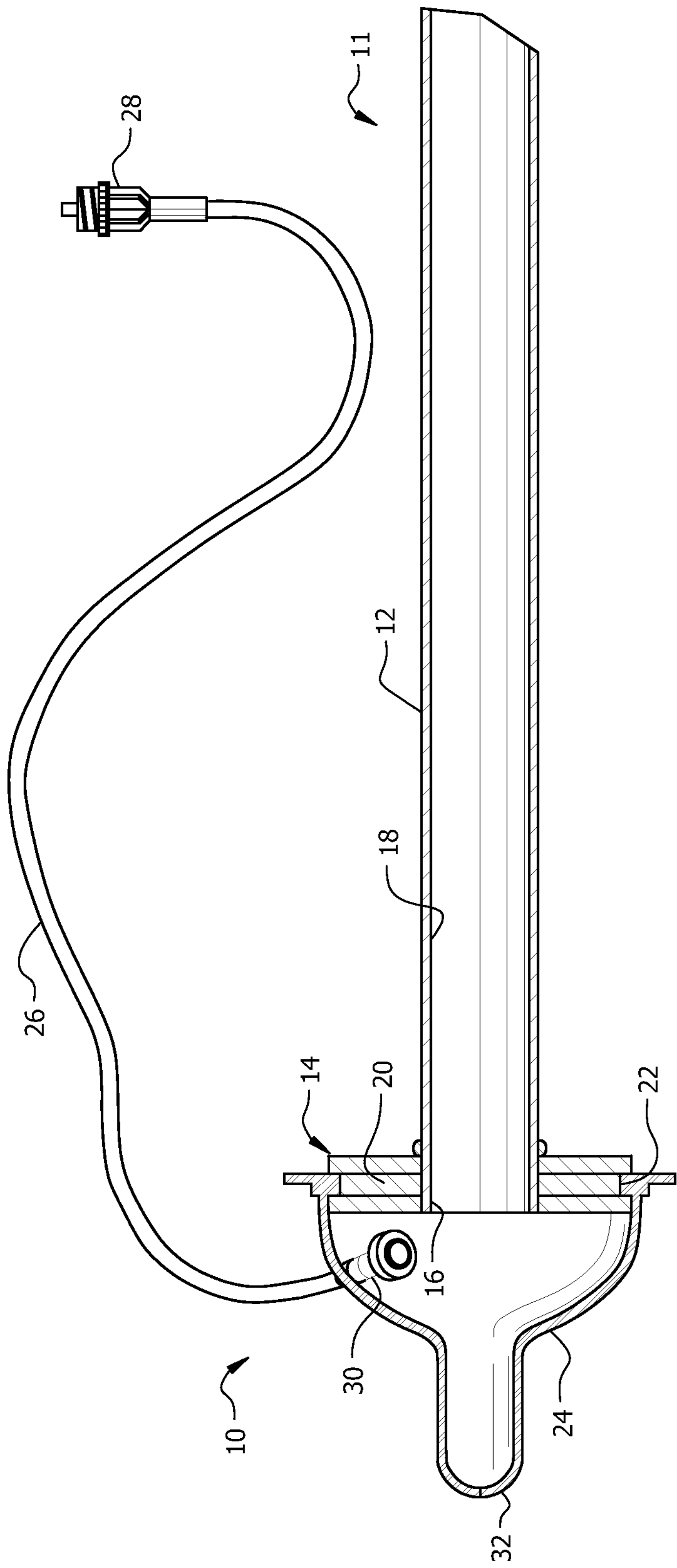
FIG. 1B is a combination perspective and longitudinal sectional view of the parts depicted in FIG. 1A.
Figure 2:
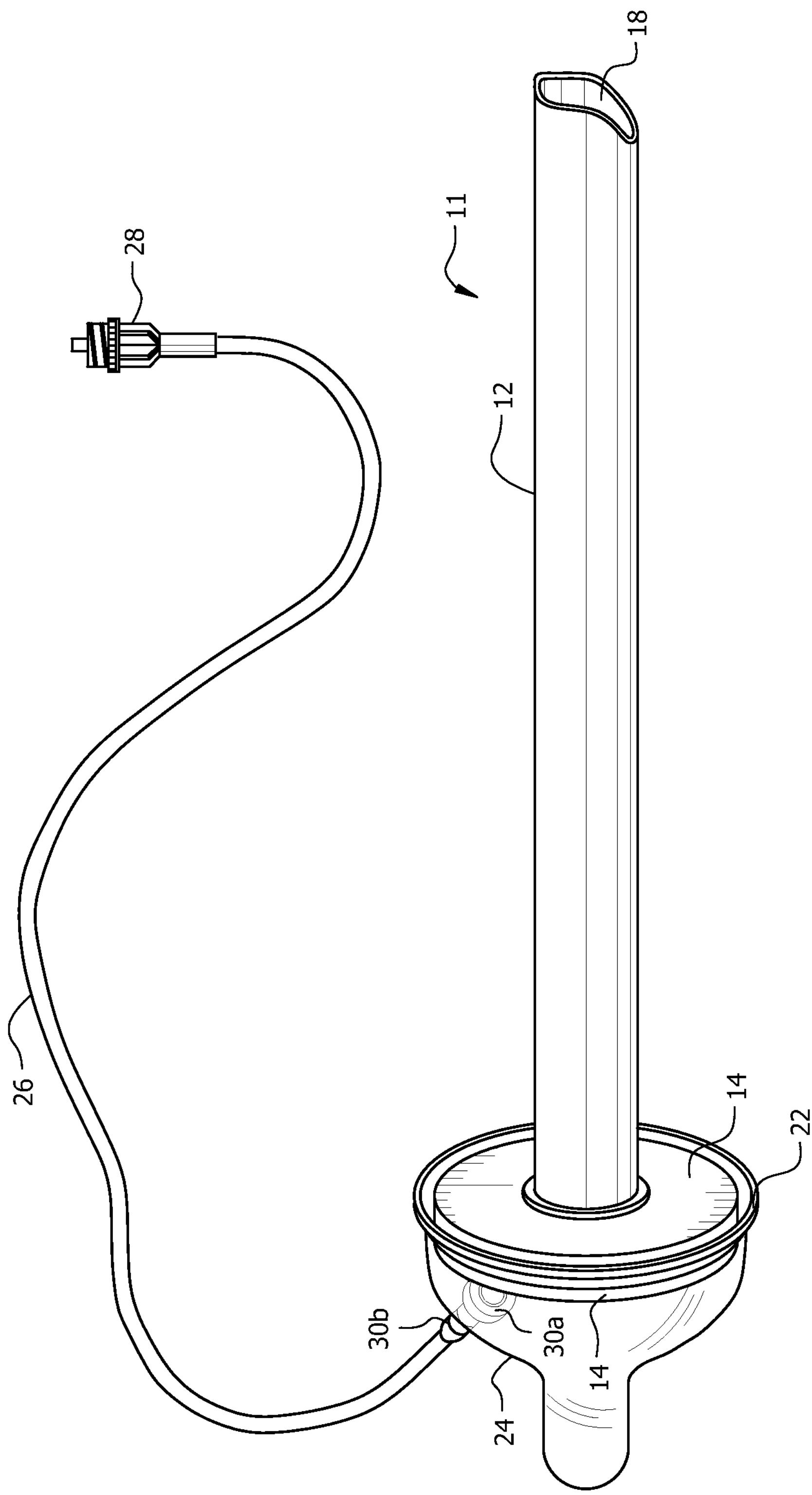
FIG. 2 is a second, rearward perspective view of the first embodiment.

Referring now to FIGS. 1A, 1B, and 2, it will there be seen that an illustrative embodiment of the invention is denoted as a whole by the reference numeral 10.

Cannula 11 includes an elongate, tubular main body 12, a disc-shaped hollow hub 14 at the proximal end of said tubular main body, and a central aperture 16 formed in said hub. As depicted in FIG. 1B, the proximal end of tubular main body 12 is slideably disposed within central aperture 16 as depicted.

Annular groove 20 is formed in the outer periphery of hub 14; it has a substantially square contour.

Annular ridge 22 is integrally formed in the wide distal end of flexible, plastic nipple 24 and is adapted to engage annular groove 20. Nipple 24 has an elongate, narrow proximal end.

Nipple 24 and similar nipples are commercially available under the trademark PLAYTEX® nipples and their equivalents. Annular ridge 22 is formed on an interior surface of said nipple and has a square contour that substantially matches the square contour of annular groove 20.

The diameter of annular ridge 22 is slightly less than the diameter of hub 14 so that nipple 24 must be stretched to enable annular ridge 22 to enter annular groove 20. When annular ridge 22 is seated in groove 20, the seal is tight and will not leak when gas under pressure is introduced into the hollow interior of the nipple. An adhesive may also be used to enhance the annular seal.

Elongate hose 26 provides fluid communication between a remote gas machine, not depicted, and nipple 24. Hose connector 28 is secured to the proximal end of hose 26 and said hose connector engages stop cock valve, not depicted in FIGS. 1 and 2, that provides an interface between an outlet port of said gas machine and the proximal end of said elongate hose.

Compression fitting 30 extends snugly through a small gas opening formed in nipple 24. It includes a base 30*a* having a diameter substantially greater than the diameter of the small opening and a post 30*b* formed integrally with base 30*a* and having a diameter greater than the diameter of the lumen of elongate hose 26. Base 30*a* is positioned within the space defined by hub 14 of cannula 11 and nipple 24 and post 30*b* is positioned externally of said nipple. Annular ridges are formed on post 30*b*; the ridges are angled to facilitate sliding attachment of the distal end of elongate hose 26 onto said post and to prevent facile detachment of said distal end from said post.

In this first embodiment, valve 32 is formed in the narrow proximal end or tip of nipple 24. Various preselected surgical instruments may be introduced into the lumen of cannula 10 through said valve. The valve seals around the periphery of the preselected surgical instrument to inhibit leakage of gas and said valve seals the nipple against gas leakage when a surgical instrument is withdrawn from said cannula and attached nipple because the material of which nipple 24 is made is resilient.

Valve 32 may be provided in the form of a duckbill valve as well, or in the form of a cross-slit valve. Examples of such valves may be seen at minivalve.com.

Nipple 24 is mass produced at a very low cost for use on baby bottles and thus its use in this environment represents a substantial cost savings over conventional means for interconnecting a gas machine to a cannula.

Figure 3A:
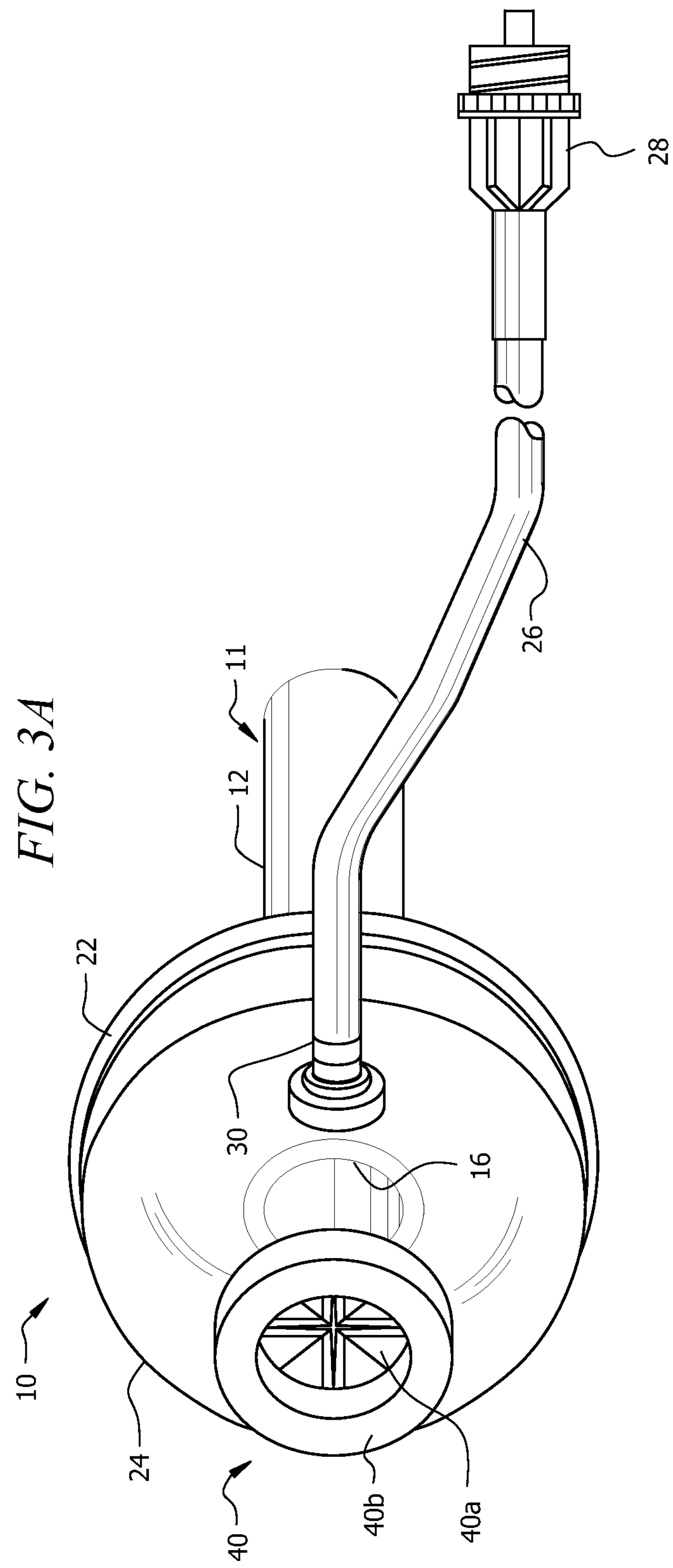
FIG. 3A is a perspective view of a second embodiment.
Figure 3B:
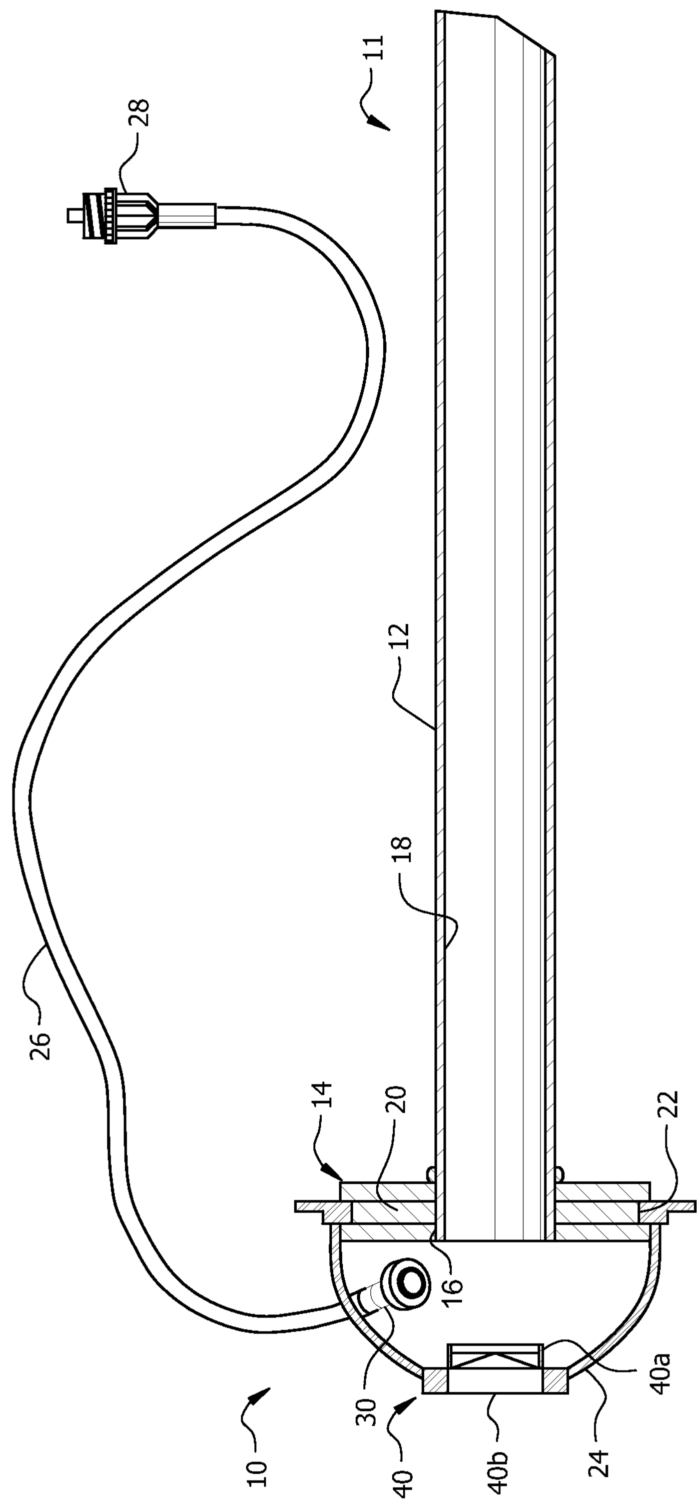
FIG. 3B is a combination perspective and longitudinal sectional view of the embodiment of FIG. 3A.

The second embodiment is depicted in FIGS. 3A and 3B. Baby bottle nipple 24 is used in this embodiment but the narrow leading end of the nipple is cut off at its base to create a circular opening. A valve means such as cross-slit valve 40, a duckbill valve, or other suitable valve means is seated in said opening as depicted in FIG. 3A but perhaps better understood in connection with FIG. 3B.

This second embodiment works in the same way as the first embodiment but the use of valve means 40 may enhance the seal around a surgical instrument inserted into lumen 18 of cannula main body 12.

However, forming a cut or cuts such as slits 32 in the narrow proximal end of nipple 24 to form a leak-proof valve as in the first embodiment may be more cost-effective than cutting off said narrow proximal end at its base and installing a pre-manufactured valve.

Figure 4:
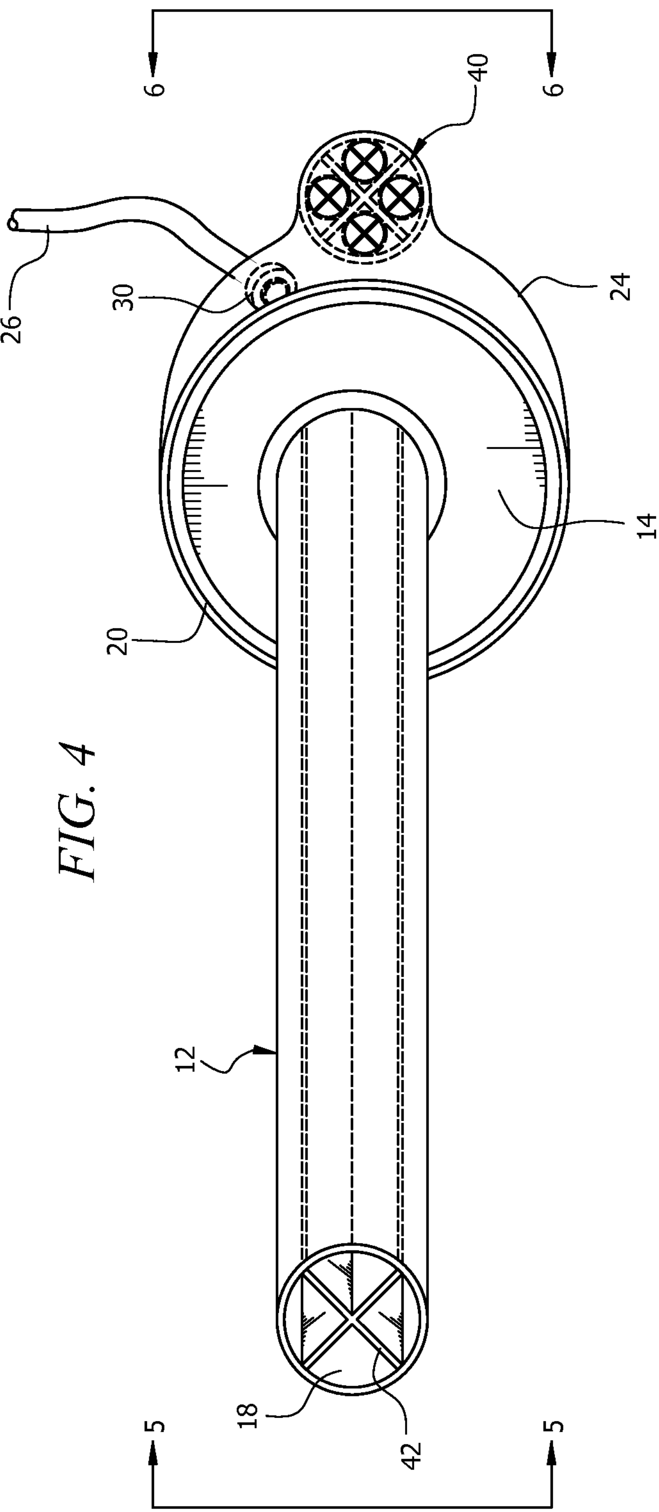
FIG. 4 is a perspective view of a third embodiment where the lumen of the cannula is subdivided into four (4) chambers by a partition member.

A third embodiment is depicted in FIGS. 4-6. It can be used with the first or second embodiments but works best with the second embodiment. As best understood in connection with FIG. 4, lumen 18 of cannula 12 is subdivided by partition member 42 that preferably extends the entire extent of said lumen but which may be shortened to save materials. In this example, the lumen is divided into four (4) compartments or sub-lumens of substantially equal size because partition member 42 has the shape of a plus sign (+) or an “X” depending upon its angular orientation. The lumen could be divided in half by a flat partition member or into three (3) compartments by a "Y"-shaped partition member. It is also within the scope of this invention to subdivide the lumen into five or more sub-lumens.

FIG. 5 provides a front end view of the third embodiment and FIG. 6 provides a rear end view thereof. As depicted in FIGS. 4-6, each subdivided lumen is associated with and in axial alignment with a valve 40 similar to valve 40 of the second embodiment, only smaller. However, any suitable valve, including a slit valve 32 as in the first embodiment, may also be used. Four (4) surgical instruments may therefore be introduced into cannula 12 at the same or different times and each of them is independently sealed at its proximal end by a dedicated valve means 40. The surgical instruments may include an endoscope, a camera, an illumination means, an irrigation means, and so on.

It is also possible to use the baby bottle nipple of the first embodiment, with its narrow proximal end intact, in conjunction with a subdivided lumen of the type provided in connection with the third embodiment. Additional valve means are formed in the intact nipple at locations thereon that are in axial alignment with a sub-lumen. As in all embodiments, the number of sealing valves formed in the nipple should equal the number of lumens provided.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween. Now that the invention has been described,

What is claimed is:

1. A method for delivering gas to an abdominal cavity, comprising the steps of:

providing a cannula comprising:

an elongate, tubular main body having a lumen;

a thin, flat disc-shaped hub connected to a proximal end of said elongate, tubular main body;

a central aperture formed in said thin, flat disc-shaped hub;

said central aperture slideably receiving said proximal end of said elongate, tubular main body;

an annular groove formed in an outer periphery of said thin, flat disc-shaped hub;

a staple item of commerce in the form of a conventional baby bottle nipple having a radially-inwardly extending annular ridge formed therein;

said conventional baby bottle nipple formed of a flexible and resilient material;

said radially-inwardly extending annular ridge having a diameter slightly less than a diameter of said annular groove so that said annular groove releasably but snugly receives said radially-inwardly extending annular ridge;

at least one sealable valve formed in said conventional baby bottle nipple; and an elongate hose adapted to provide fluid communication between a remote gas machine and an enclosed space defined by said conventional baby bottle nipple and said thin, flat disc-shaped hub when said conventional baby bottle nipple is attached to said thin, flat disc-shaped hub; and delivering gas under pressure to an abdominal cavity of a patient through said elongate hose, said enclosed space, and said lumen.

2. The method of claim 1, further comprising:

said conventional baby bottle nipple including a narrow proximal end and a wide distal end:

said wide distal end including said radially-inwardly extending annular ridge.

3. The method of claim 1, further comprising:

said annular groove having a square contour in transverse cross-section; and said annular ridge having a square contour in transverse cross-section.

4. The method of claim 3, further comprising:

an adhesive applied to said annular groove and radially-inwardly extending annular ridge for enhancing a seal between them.

5. The method of claim 2, further comprising:

said at least one sealable valve being formed in said narrow proximal end of said conventional baby bottle nipple and being adapted to slidingly receive preselected surgical instruments;

said at least one sealable valve adapted to seal around the periphery of a preselected surgical instrument to inhibit leakage of gas when a preselected surgical instrument is positioned in said at least one sealable valve; and said at least one sealable valve adapted to seal said conventional baby bottle nipple against gas leakage when a preselected surgical instrument is withdrawn from said at least one sealable valve.

6. The method of claim 5, further comprising:

said at least one sealable valve being in the form of a duckbill valve.

7. The method of claim 5, further comprising:

said at least one sealable valve being in the form of a cross-slit valve.

8. The method of claim 5, further comprising:

said at least one sealable valve including a plurality of sealable valves formed in said narrow proximal end of said conventional baby bottle nipple.

9. The method of claim 8, further comprising:

a partition member dividing said lumen into at least two sub-lumens so that at least two preselected surgical instruments can be introduced into said two sub-lumens through at least two of said plurality of sealable valves.

10. The method of claim 9, further comprising the steps of:

said partition member having a length substantially equal to a length of said lumen.

11. The method of claim 9, further comprising:

said partition member having a plus sign shape and dividing said lumen into four sub-lumens of substantially equal size;

said plurality of sealable valves including four sealable valves in substantial axial alignment with said four sub-lumens.

12. The method of claim 2, further comprising:

a hose connector secured to a proximal end of said elongate hose;

said hose connector adapted to engage said remote gas machine;

a small opening formed in said wide distal end of said conventional baby bottle nipple;

a fitting that extends snugly through said small opening;

said fitting including a base having a diameter substantially greater than a diameter of said small opening;

said fitting including a post formed integrally with said base;

said post having a diameter greater than a diameter of the lumen of said elongate hose;

said base being positioned within a space defined by said thin, flat disc-shaped hub and said conventional baby bottle nipple and said post being positioned externally of said conventional baby bottle nipple.

13. The method of claim 12, further comprising:

at least one annular ridge formed on said post;

said at least one annular ridge formed on said post being angled to facilitate sliding attachment of a distal end of said elongate hose onto said post and to prevent facile detachment of said distal end from said post.

14. The method of claim 1, further comprising:

said conventional baby bottle nipple having a hemispherical shape that includes a wide distal end and a valve-receiving opening formed in a proximal end of said conventional baby bottle nipple.

15. The method of claim 14, further comprising:

at least one sealable valve adapted to be received within said valve-receiving opening.

16. The method of claim 15 further comprising:

said at least one sealable valve including a plurality of valves; and said lumen being subdivided into as many sub-lumens as there are valves in said plurality of valves.

* * * * *